United States Patent [19]
Kim et al.

[11] Patent Number: 5,659,094
[45] Date of Patent: Aug. 19, 1997

[54] PROCESS FOR CO-PRODUCING 1,1,1,2-TETRAFLUOROETHANE PENTAFLUOROETHANE AND 1,1,1-TRIFLUOROETHANE

[75] Inventors: Hoon Sik Kim; Byung Gwon Lee; Honggon Kim; Moon Jo Chung, all of Seoul, Rep. of Korea

[73] Assignee: Korea Institute of Science and Technology, Seoul, Rep. of Korea

[21] Appl. No.: 591,705

[22] Filed: Jan. 25, 1996

[30] Foreign Application Priority Data

Aug. 23, 1995 [KR] Rep. of Korea ............... 26126/1995

[51] Int. Cl.$^6$ ............... C07C 19/08; C07C 17/20; C07C 17/21
[52] U.S. Cl. ............... 570/168; 570/166; 570/169; 570/170
[58] Field of Search ............... 570/166, 168, 570/169, 170

[56] References Cited

U.S. PATENT DOCUMENTS

| | | | |
|---|---|---|---|
| 3,258,500 | 6/1966 | Swamer et al. | 570/169 |
| 4,091,043 | 5/1978 | Ohsaka et al. | 570/170 |
| 4,129,603 | 12/1978 | Dell | 570/169 |
| 4,990,701 | 2/1991 | Cassel et al. | 570/170 |
| 4,990,702 | 2/1991 | Fernandez et al. | 570/170 |
| 5,281,568 | 1/1994 | Scott et al. | 502/307 |
| 5,494,873 | 2/1996 | Tsuji et al. | 502/319 |
| 5,494,876 | 2/1996 | Tsuji et al. | 502/224 |
| 5,494,877 | 2/1996 | Katsuyuki et al. | 502/228 |
| 5,500,400 | 3/1996 | Kim et al. | 502/306 |
| 5,523,498 | 6/1996 | Manzer et al. | 570/156 |
| 5,569,795 | 10/1996 | Tsuji et al. | 570/168 |

FOREIGN PATENT DOCUMENTS

| | | |
|---|---|---|
| 0 449 617 A2 | 10/1991 | European Pat. Off. |
| 29 32 934 A1 | 8/1978 | Germany. |
| 83402 | 7/1977 | Japan. |
| 2-178237 | 7/1990 | Japan. |
| 4-29940 | 1/1992 | Japan. |
| 91-16657 | 11/1991 | Rep. of Korea. |

*Primary Examiner*—Alan L. Rotman
*Attorney, Agent, or Firm*—Darby & Darby

[57] ABSTRACT

A process for co-production of 1,1,1,2-tetrafluoroethane (HFC-134a; $CF_3CH_2F$), pentafluoroethane (HFC-125; $CF_3CHF_2$) and 1,1,1 -trifluoroethane (HFC-143a; $CF_3CH_3$) by a two-step gaseous reaction comprising the steps of a) reacting 1,1,1-trifluoro-2-chloroethane ($CFCH_2Cl$, HCFC-133a) with HF in a first reactor to prepare 1,1,1,2-tetrafluoroethane (HFC-134a; $CF_3CH_2F$), pentafluoroethane (HFC-125; $CF_3CHF_2$) and 1,1,1-trifluoroethane (HFC-143a; $CF_3CH_3$); b) adding trichloroethylene (TCE:$CCl_2CHCl$) to the reaction product of step a) in a second reactor to prepare HCFC-133a; separating HCl, HFC-134a, HFC-125 and HFC-143a from the reaction product of step b) and recycling HCFC-133a to the first reactor, and the stages being performed in the presence of fluorization catalyst obtained by calcining a reaction product which is obtained by reacting ethanol with a mixture of calcium fluoride($CaF_2$) with an aqueous solution of chromium trioxide, zinc chloride and ferrous chloride is provided.

8 Claims, No Drawings

PROCESS FOR CO-PRODUCING 1,1,1,2-TETRAFLUOROETHANE PENTAFLUOROETHANE AND 1,1,1-TRIFLUOROETHANE

BACKGROUND OF THE INVENTION

1. Field of the Invention

The present invention relates to a novel method for manufacturing an a catalyst for co-producing 1,1,1,2-tetrafluoroethane ($CF_3CH_2F$, hereinafter refers to HFC-134a), pentafluoroethane($CF_3CHF_2$, herein after refers to HFC-125), and 1,1,1-trifluoroethane ($CF_3CH_3$, hereinafter refers to HFC-143a) simultaneously, and also a process for co-producing HFC-134a, HFC-125, and HFC-143a by two-step gaseous phase reaction using the said catalyst. Specifically, the present invention relates to a method that characterized in that in the first step, 1,1,1-trifluoro-2-chloroethane($CF_3CH_2Cl$, hereinafter HFC-133a) is reacted with hydrogenfluoride(HF) in the presence of catalyst which comprising iron, nickel, chromium and zinc compound, to obtain HFC-134a, HFC-125 and HFC-143a and then, at the second step, trichloroethylene($CCl_2CHCl$, hereinafter TCE) is added to the said reaction product of the first step to obtain HCFC-133a and then, HFC-134a, HFC-125, and HFC-143a are separated and HCFC-133a is recycled to the first step reaction.

2. Description of the Prior Art

It has been revealed that CFC(Chlorofluorocarbon) widely used as coolant, cleaning agent, and blowing agent, is a primary factor of destroying the ozone layer in stratosphere. Therefore, its production and use has been restricted under the international agreement. As a result of testifying widely the toxicity, safety, and physical and chemical efficiency of the target material for a long time to develop a material which can be substituted for these CFC compounds, it has been known that compounds such as difluoromethane (HFC-32), trifluoromethane(HFC-23), 1,1-difluoroethane (HFC-152a), 1,1,1,2-tetrafluoroethane(HFC-134a), pentafluoroethane (HFC-125), 1,1,1-trifluoroethane and like are favorable CFC substitutes. Among these, HFC-134a has been studied for mass production as a prominent substitute for dichloromethane(CFC-12) which has been used as an essential coolant. But other materials have not been researched sufficiently for use and it is tried to use as a special coolant as mixed one another. For example, the research has been made for a mixture of HFC-134a, HFC-32 and HFC-143a, and a mixture of HFC-134a, HFC-32 and HFC-125 as low temperature coolant for practice.

The methods for producing HFC-134a are disclosed in EP No. 0 449 617 A2 and Korea Patent Laid-Open No. 91-16657 and so forth. In EP No. 0 449 617 A2, TCE and HF are used as starting materials and HFC-134a is manufactured by two step reaction method. In Korea Patent Laid-open No. 91-16657, it is disclosed that reaction temperature is easily controlled and the formation of 1,1-difluoro-2-chloroethylene($CF_2CHCl$, HCFC-1122) is suppressed by feeding the inactive gases into reactor when HFC-134a is produced by two-step using TCE and HF as the starting materials.

According to U.S. Pat. No. 4,129,603, chromium hydroxide is treated under steam condition and then, converted to chromium oxyfluoride form by hydrogen fluoride and this is used for manufacturing HFC-134a. But this method has a default that HCFC-1122($CF_2CHCl$), which is difficult to separate from HFC-134a, is produced in large amount as a by-product and a supplemental reactor is needed to remove thereof.

In DE Patent No. 29 32 934, chromium fluoride or chromium oxyfluoride is used as a catalyst. It shows a high selectivity about 98% around reaction temperature of 400° C. but its activity is lowered after 44 hours. As oxygen is supplied continuously together with reactants, separation of HCl produced is difficult and the corrosion of apparatus is accelerated by moisture. Therefore this method is disadvantageous to be processed.

Several methods for producing HFC-125 are disclosed; methods that tetrachloroethylene($CCl_2CCl_2$) is reacted with HF on a catalyst comprising alumina and chromium as main components are disclosed in Japan Patent Laid-Open No. 90-178237 and U.S. Pat. No. 3,258,500; and a method that HCFC-122 ($CF_2ClCHCl_2$) is fluorinated on a catalyst mainly consisting of alumina, in the presence of oxygen to obtain HCFC-123($CF_3CHCl_2$), HCFC-124($CF_3CHClF$) and HFC-125($CF_3CHF_2$) is described in Japan Patent Laid-Open No. 92-29940. But these methods are not economic due to a low selectivity to HFC-125 and yielding a large amount of side product.

As a process for manufacturing HFC-143a, it is proposed in Japan Patent Publication No. 84-46211 and U.S. Pat. No. 4,091,043 that 1,1,1-trichloroethane($CCl_3CH_3$) is reacted with HF in the presence of $SbCl_5$ to produce HCFC-142b and HFC-143a simultaneously. And it is also described that among the reaction products HFC-143a can be obtained up to about 80% by the method.

SUMMARY OF THE INVENTION

The object of the present invention provides a catalyst which can produce HFC-134a, HFC-125 and HFC-143a simultaneously and process for co-producing thereof. As an enormous investment for equipment is required to establish a plant for producing CFC substitutes, a risk bearing is involved in the establishment of large scale plant for manufacturing CFC substitutes of which the demand is not expected to be highly increased in the near future.

The present invention provides a catalyst that can produce the above materials simultaneously and also provides a process for co-producing thereof in a single plant. Therefore, the present invention provides an economical way of producing these compounds, while controlling the production ratio according to the change of demands without further plant building.

DETAILED DESCRIPTION OF THE INVENTION

According to the present invention, calcium fluoride ($CaF_2$) is mixed with an aqueous solution of chromium trioxide($CrO_3$), zinc chloride($ZnCl_2$) and ferrous chloride ($FeCl_2$) and then, the reaction product of the resultant mixture with ethanol is calcined to provide a catalyst that can be maintain its activity for a long time without supply of oxygen during fluorination. When a chromium oxide catalyst is used for producing HFC-134a, it is necessary to supply oxygen to prevent a sudden drop of catalytic activity. But, when the catalyst of the present invention is used, it does not require the oxygen supply for the maintenance of catalytic activity and as a result, it is much easier to separate HCl. In addition, there is no unnecessary HCl oxidation due to oxygen and the possibility of existing water in system will be lowered. So the duration ability of apparatus against corrosion can de enhanced. Furthermore, the catalyst according to the present invention has an excellent activity to a heterogeneous reaction of HCFC-133a and advantageous to obtain HFC-125 and HFC-143a simultaneously by the heterogeneous reaction between HCFC-133a and HF.

The process for co-producing HFC-134a, HFC-125 and HFC-143a using the catalyst of the present invention is described more concretely as follows.

HCFC-133a($CF_3CH_2Cl$) and HF are fed into a first reactor, and HCFC-133a is reacted with HF to produce HFC-134a ($CF_3CH_2F$) as reaction equation (1) or disproportioned into HFC-143a($CF_3CH_3$) and HCFC-123 ($CF_3CHCl_2$) as reaction equation (2). The produced HCFC-123 reacts with HF to yield HCFC-124($CF_3CHClF$) and HFC-125($CF_3CHF_2$) as reaction equation (3)–(4). The reaction mixture from the first reactor is feeded with additionally supplied TCE($CCl_2CHCl$) into the second reactor, and in the second reactor, HCFC-133a is produced according to reaction equation (5). The reaction product eluded out from the second reactor is recycled to the first reactor after the separation of HCl, HFC-134a, HFC-125 and HFC-143a.

$$CF_3CH_2Cl + HF \rightarrow CF_3CH_2F + HCl \quad (1)$$

$$2CF_3CH_2Cl \rightarrow CF_3CH_3 + CF_3CHCl_2 \quad (2)$$

$$CF_3CHCl_2 + HF \rightarrow CF_3CHClF + HCl \quad (3)$$

$$CF_3CHClF + HF \rightarrow CF_3CHF_2 + HCl \quad (4)$$

$$CCl_2CHCl + 3HF \rightarrow CF_3CH_2Cl + 2HCl \quad (5)$$

The molar ratio of Cr to Ca of the catalyst according to the present invention is suitably 1:0.5 to 1:16 and preferably within the range of 1:1 to 1:8. The molar ratios of Fe to Cr and Zn to Cr are 0.05–0.8, respectively, and preferably within the range of 0.1–0.5.

The temperature of the first reactor according to the present invention is suitable within the range of 300°–450° C. and preferably within the range of 320°–400° C. The contact time is in the range of 1–60 seconds, and preferably in the range of 5–30 seconds. Though the molar ratio of HF/133a can be performed in the range of 1–30, it is good to handle the molar ratio of HF/133a in the range of 4–10 to enhance the yield of HFC-125 and HFC-143a which can be resulted from the heterolysis reaction between HCFC-133a's. When the molar ratio of HF/133a is lower than 4, the lifespan of the catalyst may be shortened. When the molar ratio of HF/133a is higher than 10, it is no more economic due to the reduction of productivity.

The temperature of the second reactor, is within the range of 200°–400° C. and preferably within the range of 230°–320° C. The contact time is in the range of 1–20 seconds, and preferably in the range of 2–6 seconds. The molar ratio of HF/TCE is in the range of 1–30 and it is good to handle the molar ratio of HF/TCE in the range of 20–40.

The reaction pressure according to the present invention is controlled in the range of 7–10 kg/cm$^2$ to separate the yielded HCl smoothly. As materials for the reaction apparatus, nickel-200/201 or Inconell-600(Inco Alloy International) which can stand with corrosive materials such as HCl and HF is suitable.

The apparatus used in the Example of the present invention is as follows. The first and the second reactors consist of single cylinderic-form reactor made from Inconell having a capacity of 500 cc and 150 cc, respectively. And the first reactor is filled with 500 g of catalyst and the second with 150 g. An evaporator, a pre-heater and a distillation tower are used as supplemental apparatus. The reactor is installed inner side of the cylinderical electric furnace equipped with automatic temperature controller and the starting materials are feeded into the reactor using metering pump to control the flow. All starting materials are supplied into the reactor in gaseous phase by setting up a pre-heater just prior to the first reactor, and the outlet temperature of the pre-heater is controlled to be equal to the predetermined temperature of the inlet of the first reactor. The reaction product outlet from the first reactor is mixed with liquid phase raw material additionally supplied from the evaporator, and then, feeded into the second reactor in gaseous phase. The outlet temperature of the evaporator is controlled to be equal to the predetermined temperature of the inlet of the second reactor.

In the present invention, conversion of HCFC-133a, selectivity of HFC-134a, HFC-125 and HFC-143a are defined as follows.

Conversion(%) of HCFC-133a=(HCFC-133a reacted/HCFC-133a supplied)×100

Selectivity(%) of HFC-134a=(HFC-134a produced/HCFC-133a reacted)×100

Selectivity(%) of HFC-125=(HFC-125 produced/HCFC-133a reacted)×100

Selectivity(%) of HFC-143a=(HFC-143a produced/HCFC-133a reacted)×100

EXAMPLE 1

Preparation of Catalyst

In a 5-liter flask provided with condenser and stirrer, a mixture of $CrO_3$ (300 g), $FeCl_2$ (150 g), $ZnCl_2$ (140 g) and $CaF_2$ (940 g) was dissolved in 1800 cc of water, and 95% ethanol (300 cc) was added thereto with stirring over about four hours. After slowly raising the temperature of the reaction mixture up to 90° C., the mixture was refluxed while maintaining the temperature for 16 hours. The temperature was lowered to room temperature, and precipitates obtained by filtration was dried at 120° C. for 5 hours. The dried catalyst was calcined at 300° to 400° C. for 5 hours, and formed as a cylindrical pellet (4 mm×4 mm) to use in the reaction.

EXAMPLE 2–7

Catalysts were prepared according to the same procedure as Example 1, but the weight ratio of Cr, Ca and metal components were changed as shown in Table 1 below.

TABLE 1

| The composition of the prepared catalyst | |
|---|---|
| Example | Composition of Catalyst (molar ratio) |
| 2 | Cr:Ca:Fe:Zn = 1:1:0.1:0.1 |
| 3 | Cr:Ca:Fe:Zn = 1:3:0.2:0.2 |
| 4 | Cr:Ca:Fe:Zn = 1:6:0.4:0.4 |
| 5 | Cr:Ca:Fe:Zn = 1:8:0.5:0.5 |
| 6 | Cr:Ca:Fe:Zn = 1:4:0.5:0.1 |
| 7 | Cr:Ca:Fe:Zn = 1:1:0.1:0.2 |

EXAMPLE 8

HCFC-133a and HF was mixed in a flow rate of 0.7 g-mol/hr and 10 g-mol/h, respectively, and the mixture supplied via preheater to the first reactor, using the catalyst prepared in Example 1. The contacting time of the first reactor was about 7 sec. based upon ambient temperature and pressure. The reaction temperature was maintained at 360° C., and the pressure at 8 atm. The molar compositions of organic compounds in the reaction product flowed out from the first reactor are as follows:

HCFC-133a 73.6%, HFC-134a 20.6%, HFC-125 2.8%

HFC-143a 2.7%, HCFC-124 0.2%, HCFC-123 0.1%

Analysing the results obtained, the conversion of HCFC-133a is 26.4%, selectivity of HFC-134a is 78.0%, that of HFC-125 is 10.6%, and that of HFC-143a is 10.2%. The reaction product flowed out from the first reactor was mixed with TCE of flow rate 0.5 g/mol/hr in a vaporizer, and the mixture was supplied into the second reactor. The temperature of the second reactor was maintained at 240° to 300° C. The molar compositions of organic compounds in the final reaction product flowed out from the second reactor are as follows:

HCFC-133a 81.5%, HFC-134a 13.7%, HFC-125 1.5% HFC-143a 1.4%, HCFC-124 0.2%, HCFC-123 0.0% others 0.2%

EXAMPLE 9–17

The same procedure was carried out with the same apparatus as Example 1, only varing the type of catalysts and reaction conditions as shown in Table 2:

HCFC-133a to the first reactor, and the steps being performed in the presence of fluorization catalyst obtained by calcining a reaction product which is obtained by reacting ethanol with a mixture of calcium fluoride($CaF_2$) with an aqueous solution of chromium trioxide($CrO_3$), zinc chloride($ZnCl_2$) and ferrous chloride($FeCl_2$).

TABLE 2

Change of conversion ratio of HCFC-133a and selectivity of HFC-134a, HFC-125, HFC-143a, dependent upon type of catalysts and reaction conditions.

| Example | catalyst used | 1st reactor's reaction condition | | | 133a conversion (%) | 134a selectivity (%) | 125 selectivity (%) | 143a selectivity (%) | 2nd reactor's reaction condition | | TCE conversion (%) |
|---|---|---|---|---|---|---|---|---|---|---|---|
| | | reation temp. (°C.) | contact time (sec) | HF/133a (molar ratio) | | | | | HF/TCE (molar ratio) | contact time (sec) | |
| 9  | Ex 2 | 340 | 10 | 6.0  | 23.1 | 89.6 | 4.9  | 5.1  | 30 | 5  | 100.0 |
| 10 | Ex 3 | 340 | 15 | 10.0 | 25.3 | 82.4 | 8.5  | 8.9  | 30 | 3  | 98.0  |
| 11 | Ex 4 | 340 | 20 | 8.0  | 26.5 | 75.8 | 11.8 | 12.3 | 25 | 7  | 100.0 |
| 12 | Ex 5 | 350 | 30 | 8.0  | 30.7 | 69.7 | 14.7 | 15.2 | 25 | 10 | 100.0 |
| 13 | Ex 6 | 350 | 20 | 8.0  | 29.4 | 71.0 | 14.1 | 14.6 | 20 | 7  | 99.2  |
| 14 | Ex 7 | 350 | 15 | 7.0  | 24.9 | 81.4 | 8.9  | 9.4  | 20 | 5  | 97.3  |
| 15 | Ex 1 | 380 | 10 | 7.0  | 33.1 | 63.7 | 17.7 | 18.2 | 40 | 3  | 100.0 |
| 16 | Ex 5 | 320 | 5  | 7.0  | 15.9 | 91.6 | 3.8  | 4.2  | 35 | 2  | 98.0  |
| 17 | Ex 6 | 400 | 7  | 4.0  | 36.8 | 49.8 | 24.9 | 25.3 | 20 | 10 | 100.0 |

What is claimed is:

1. A process for co-production of 1,1,1,2-tetrafluoroethane (HFC-134a;$CF_3CH_2F$), pentafluoroethane (HFC-125; $CF_3CHF_2$) and 1,1,1-trifluoroethane (HFC-143a; $CF_3CH_3$) comprising the steps of;

a) reacting 1,1,1-trifluoro-2-chloroethane ($CFCH_2Cl$, HCFC-133a) with HF in a first reactor to prepare 1,1,1,2-tetrafluoroethane (HFC-134a; $CF_3CH_2F$), pentafluoro ethane (HFC-125; $CF_3CHF_2$) and 1,1,1-trifluoroethane (HFC-143a; $CF_3CH_3$); and b) adding trichloroethylene (TCE:$CCl_2CHCl$) to the reaction product of step a) in a second reactor to prepare HCFC-133a;

separating HCl, HFC-134a, HFC-125 and HFC-143a from the reaction product of step b) and recycling 2. A process according to claim 1, wherein a molar ratio of Cr:Ca in the fluorination catalyst is 1:1 to 1:8; that of Cr:Fe is 1:0.1 to 1:0.5; and that of Cr:Zn is 1:0.1 to 1:0.5.

3. A process according to claim 1, wherein a reaction temperature of the step a) is 320°–400° C.

4. A process according to claim 1, wherein the molar ratio of HF:HCFC-133a is 4 to 10.

5. A process according to claim 1, wherein the contact time of the step a) is 5 to 30 seconds.

6. A process according to claim 1, wherein the reaction temperature of the step b) is 230° to 300° C.

7. A process according to claim 1, wherein the contact time of the step b) is 2 to 6 seconds.

8. A process according to claim 1, the molar ratio of HF:TCE of the reaction step b) is 20 to 40.

* * * * *